United States Patent [19]

Kondo et al.

[11] Patent Number: 4,596,887

[45] Date of Patent: Jun. 24, 1986

[54] PROCESS FOR PREPARING DIHALOVINYLCYCLOPROPANECARBOXYLATES

[75] Inventors: Kiyoshi Kondo; Kiyohide Matsui, both of Kanagawa, Japan

[73] Assignee: Sagami Chemical Research Center, Kanagawa, Japan

[21] Appl. No.: 696,841

[22] Filed: Jan. 29, 1985

Related U.S. Application Data

[63] Continuation of Ser. No. 466,173, Feb. 14, 1983, abandoned, which is a continuation of Ser. No. 935,191, Aug. 21, 1978, abandoned, and Ser. No. 731,194, Oct. 12, 1976, abandoned, which is a continuation of Ser. No. 606,807, Aug. 22, 1975.

[30] Foreign Application Priority Data

Oct. 30, 1975 [JP] Japan .................. 50-131255

[51] Int. Cl.$^4$ ............................................. C07C 67/32
[52] U.S. Cl. ..................... 560/124; 260/465 D; 549/61; 549/66; 549/79; 549/496; 549/499
[58] Field of Search ............... 560/124; 260/465 D; 549/61, 66, 79, 496, 499

[56] References Cited

U.S. PATENT DOCUMENTS

| | | | |
|---|---|---|---|
| 3,123,629 | 3/1964 | Julia | 560/124 |
| 3,354,196 | 11/1967 | Julia | 560/124 |
| 3,658,879 | 4/1972 | Julia | 560/124 |
| 4,000,180 | 12/1976 | Punja | 560/124 |
| 4,214,097 | 7/1980 | Kondo | 560/213 |

OTHER PUBLICATIONS

Ritter, J. Org. Chem. 27, pp. 622–623 (1962).

Primary Examiner—Michael L. Shippen
Attorney, Agent, or Firm—Abner Sheffer; H. Robinson Ertelt; Robert L. Andersen

[57] ABSTRACT

A cyclopropanecarboxylate of the formula

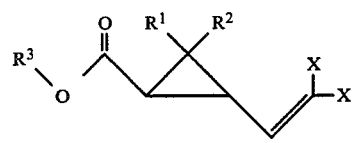

is prepared by the reaction of a compound of the formula

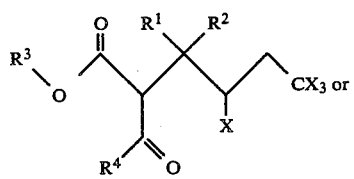

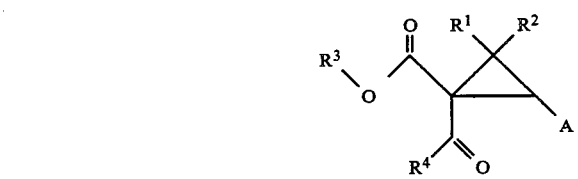

with an alkoxide in an ether type solvent. $R^1$, $R^2$, and $R^4$ each independently is hydrogen or a hydrocarbon residue, $R^3$ is an alcohol residue, X is halogen, and A is —$CH_2$—$CX_3$ or —$CH$=$CX_2$.

17 Claims, No Drawings

PROCESS FOR PREPARING DIHALOVINYLCYCLOPROPANECARBOXYLATES

This application is a continuation of application Ser. No. 466,173, filed Feb. 14, 1983, abandoned which is a continuation of application Ser. No. 935,191, filed Aug. 21, 1978, now abandoned, and Ser. No. 731,194, filed Oct. 12, 1976, now abandoned which is a continuation in part of applicants' copending application Ser. No. 606,807 filed Aug. 22, 1975.

This invention relates to a process for preparing a dihalovinylcyclopropanecarboxylate represented by the formula (I):

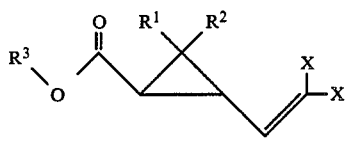

wherein $R^1$ and $R^2$ each represents a hydrogen atom or a hydrocarbon residual group, for example, a lower alkyl group, a lower cycloalkyl group, an aryl group such as phenyl or an aralkyl group such as benzyl; $R^3$ represents a lower alkyl group or a group of the formula:

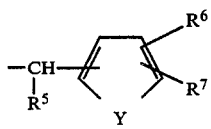

wherein Y represents an oxygen atom, a sulfur atom or a —CH=CH— group, $R^5$ represents a hydrogen atom or a cyano group, $R^6$ represents a hydrogen atom, a lower alkyl group, a phenoxy group, a benzyl group or a thiophenyl group, and $R^7$ represents a hydrogen atom or a lower alkyl group; and X represents a halogen atom. The term "lower" modifying alkyl or cycloalkyl means 1 to 6 carbon atoms, preferably 1 to 4 carbon atoms.

More specifically, this invention relates to a process for preparing a dihalovinylcyclopropanecarboxylate represented by the formula (I) above from an α-acyl-γ-halocarboxylate represented by the formula (II):

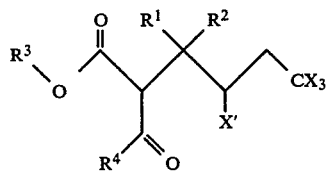

wherein $R^1$, $R^2$, $R^3$ and X are as defined above, X' is halogen of atomic number equal to or greater than X, preferably bromine or chlorine, and $R^4$ represents a hydrogen atom, a lower alkyl group, or a phenyl group.

Typical substituents for compounds of formula (II) contemplated for the process of this invention include the following:

for $R^1$ and $R^2$, each independently, hydrogen, methyl, ethyl, phenyl;

for $R^3$, methyl, ethyl, n-propyl, isopropyl, n-butyl, benzyl, 3-methylbenzyl, 3,4-dimethylbenzyl, 3-phenoxybenzyl, α-cyano-3-phenoxybenzyl, 3-phenylthiobenzyl, 3-benzylbenzyl, 5-benzyl-3-furylmethyl, 5-benzyl-2-methyl-3-furylmethyl, 5-benzylfurfuryl, 5-propargylfurfuryl, 2-methyl-5-propargyl-3-furylmethyl, 5-propargyl-2-thienylmethyl;

for $R^4$, hydrogen, methyl, ethyl, propyl, phenyl;

for $X_3$, trichloro, tribromo, trifluoro, bromodichloro, chlorodifluoro.

The α-acyl-γ-halocarboxylates represented by the formula (II) above can be obtained by addition of a carbon tetrahalide to an α-acyl-γ-unsaturated-carboxylate represented by the formula (III):

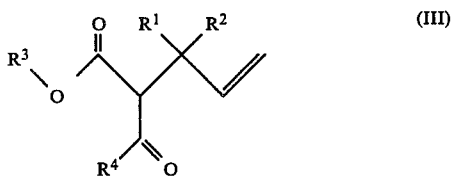

wherein $R^1$, $R^2$, $R^3$, and $R^4$, are as defined above.

Thus the object of the present invention, the preparation of the compounds of formula (I), may be carried out in one step starting with compounds of formula (II) or in two steps starting with compounds of formula (III).

The cyclopropanecarboxylates represented by the formula (I) above represent synthetic pyrethroid compounds, or intermediates which can easily be converted into these compounds, which are of interest owing to their utility as insecticides having low mammalian toxicity and long-lasting insecticidal activity [M. Elliott et al., Nature, 246, 169 (1973)].

Previously known methods for the synthesis of compounds of this type include (1) a method starting with natural chrysanthemic acid [Belgian Pat. Nos. 800,006 and 818,811 and D. G. Brown et al., J. Agr. Food Chem., 21, 767, (1973)], (2) a method comprising addition of a diazoacetic acid ester to a dihalobutadiene [J. Farkas et al., Coll. Czech. Chem. Comm., 24, 2230 (1959)], and (3) a method using, as a starting material, a 3,3-dimethyl-4-pentenoate obtainable by condensing 3-methyl-2-buten-1-ol with an orthocarboxylate [Japan Chemical Association, The 31st Autumn Annual Meeting, Preliminary Papers of Lecture Vol. I, 4A04, p58 (1974)]. However, neither method (1) nor method (2) is considered to be advantageous, since each requires an expensive starting material, expensive reagents, and a number of synthetic steps. Also, the method of (3), which is similar to the process of this invention, is not advantageous in that it requires orthocarboxylates which are not easily available as chemical industrial raw materials.

As a result of extensive studies to eliminate the disadvantages associated with the earlier methods, a general process has been found for preparing cyclopropanecarboxylates having a dihalovinyl group, a process which can be advantageously practiced on an industrial scale.

The process of this invention comprises converting an α-acyl-γ-unsaturated-carboxylate represented by the formula (III) above to the desired dihalovinylcyclopropanecarboxylate, represented by the formula (I) above, through a two-step process. The compound of the formula (III) as a starting material can be produced in accordance with known processes, for example, by condensing 3-methyl-2-buten-1-ol with an acetoacetic acid ester enol ether.

Examples of another starting material, carbon tetrahalides, are carbon tetrachloride, carbon tetrabromide, carbon monobromotrichloride, carbon dibromodichloride, carbon monoiodotrichloride, carbon difluorodichloride and the like, and most of these compounds are easily available as industrial raw materials.

In the first step of the present invention a carbon tetrahalide is added to the α-acyl-γ-unsaturated-carboxylate. In this reaction, the presence of a copper or iron salt and an organic amine in the reaction system is essential. A well-known process for adding a carbon tetrahalide to a γ-unsaturated-carboxylate comprises conducting the addition reaction in the presence of a radical reaction initiator such as azobisisobutyronitrile, benzoyl peroxide and the like, but this method is not applicable to carbon tetrahalide additions to the α-acyl-γ-unsaturated-carboxylates used in the process of this invention.

As a result of extensive study on the process for effectively conducting the addition reaction in the first step, it was found that the compound represented by the formula (II) above can be obtained selectively and effectively when a combination of a copper or iron salt and an organic amine as decribed herein is used as a catalyst. Thus, the first characteristic feature of the present invention is to use a catalyst comprising a combination of a copper or iron salt and an organic amine in the addition reaction of a carbon tetrahalide to an α-acyl-γ-unsaturated-carboxylate.

Examples of the copper salt and iron salt are cuprous chloride, cupric chloride, copper oxide, copper acetate, copper oxalate, copper hydroxide, copper acetylacetonate, copper cyanate, ferrous chloride, ferric chloride, iron oxide, iron sulfate, iron oxalate, iron citrate and the like. Examples of the organic amine are aliphatic amines such as n-butylamine, octylamine, diisopropylamine, triethylamine, cyclohexylamine, ethylenediamine and the like and aromatic amines such as aniline, toluidine and the like.

The copper or iron salt and the organic amine are considered to form a complex which functions as a catalyst for the desired reaction. Copper salts are generally superior to the iron salts from the standpoint of the reaction selectivity and the yield, and, as the organic amine, an aliphatic amine such as n-butylamine is preferred from the standpoint or availability and ability to form a complex. In order to improve the selectivity and the conversion ratio, the organic amine is used in an amount more than 1.5 mols, preferably more than 2 mols, per mol of the copper salt or the iron salt. The copper or iron salt amine complex can be used in a catalytic amount, about 0.01% based on the number of moles of α-acyl-γ-unsaturated carboxylate, but higher concentrations, 10% or more, may be used to advantage.

In carrying out the first step, the starting materials are used in equimolar amounts or the carbon tetrahalide is used in slight excess. The use of solvents is not necessarily required, but substances which do not adversely affect the reaction, for example, acetonitrile, dimethylformamide, alcohols, water, benzene, hexane and the like, can be used as a reaction medium. Also, the reaction can be conducted using an excess amount of the carbon tetrahalide starting material as a solvent. The desired reaction proceeds smoothly at a reaction temperature in the range of from 60° to 200° C., preferably from 100° to 150° C.

The second step of the process of this invention comprises, as an essential requirement, treating an α-acyl-γ-halocarboxylate represented by the formula (II) above with an alkali metal alkoxide in an ether type solvent. This requirement of the present invention was found as a result of extensive study of reaction conditions for converting the α-acyl-γ-halocarboxylates through treatment with a base into the dihalovinylcyclopropanecarboxylates represented by the formula (I), which are the desired products of the present process.

For example, when the ester represented by formula (II) above is treated in an alcohol with an alkali metal alkoxide, the main product is an ester represented by the formula (IV) below, for example, a 2-(2,2-dihalovinyl)-3,3-dimethyl-1-acylcyclopropanecarboxylate. When potassium hydroxide or sodium hydroxide is used as a base in the above reaction, the ester moiety is cleaved to produce a ketone represented by the formula (V) below, for example, a 2-(2,2-dihalovinyl)-3,3-dimethylcyclopropyl ketone is produced as a main product. Further, when a base having a low basicity is used, an ester represented by the formula (VI) below, for example, a 2-(2,2,2-trihaloethyl)-3,3-dimethyl-1-acylcyclopropanecarboxylate may be produced as a main product:

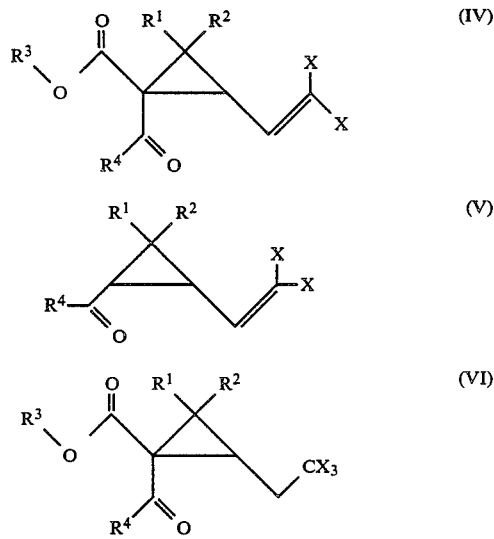

In each of formulas (IV), (V), and (VI) $R^1$, $R^2$, $R^3$, $R^4$, and X are as defined above.

Thus, it is not easy to obtain selectively as the major product the desired cyclopropanecarboxylate (I) by merely treating an α-acyl-γ-halocarboxylate (II) with a base, but the desired product (I) can be obtained selectively under the reaction conditions described herein, i.e., by treatment with an alkali metal alkoxide in an ether-type solvent. Thus, the second characteristic feature of this invention is based on the above reaction conditions.

It has also been found that the reaction conditions of the second step may also be used to convert compounds of formula (IV) or formula (VI) to the desired cyclopropanecarboxylates of formula (I).

Examples of the ether-type solvent used in the second step include those easily available as industrial solvents, such as diethyl ether, tetrahydrofuran, dioxane and the like, but it is preferred to use tetrahydrofuran from the standpoint of ease in handling and reaction efficiency. Examples of the alkali metal alkoxide are those generally used, such as sodium methoxide, potassium methoxide, sodium ethoxide, potassium ethoxide, sodium t-butoxide, potassium t-butoxide and the like. However, when $R^3$ in the formula (II) represents a lower alkyl group, it is preferred to use an alkali metal alkoxide derived from the same alcohol as the alcohol residue in the compound of the formula (II) in order to avoid mixed products owing to transesterification.

Also, when $R^3$ represents a group other than a lower alkyl group, the use of an alkali metal salt of an alcohol having the same alcohol residue as that of $R^3$ is preferred, since such an alkali metal salt makes it possible to produce the desired product (I) efficiently. However, if such an alcohol is expensive or is difficult use, the second step can be accomplished using an alkali metal alkoxide derived from t-butanol, isopropanol and the like which does not easily undergo transesterification.

The alkali metal alkoxide is used in an amount more than 2 mol equivalents, preferably 3 to 5 mol equivalents, based on the starting material (II). Also, the reaction temperature will usually be selected from the range of from about 0° C. to the reflux temperature of the solvent, based on the reaction rate and stability of the product.

The present invention is further illustrated in greater detail by the following Examples. Temperatures are in degrees centigrade. Where in spectra are given, only the frequencies of the most prominent absorption maxima appear. Tetramethylsilane was employed as an internal standard for the nmr spectra. In reporting the nmr data the abbreviations have the following significance: s, singlet; d, doublet; t, triplet; q, quartet; m, multiplet. Any of these abbreviations may be preceded by b for broad or d for double, for example, d.d., double doublet; b.t., broad triplet.

EXAMPLE 1

Synthesis of Ethyl
2-Acetyl-4,6,6,6-tetrachloro-3,3-dimethylhexanoate

The starting material, ethyl 2-acetyl-3,3-dimethyl-4-pentenoate, was prepared as follows. To a mixture of 18.5 g of 3-methyl-2-buten-1-ol and 31.0 g of ethyl β-ethoxycrotonate was added 50 mg of phosphoric acid. The resulting mixture was heated to a temperature of 150° C. over a period of about one hour and held at that temperature for 4 hours with stirring while the ethanol formed during the reaction was distilled off. Thereafter, the reaction mixture was distilled to give 33 g (84% yield) of ethyl 2-acetyl-3,3-dimethyl-4-pentenoate, boiling point 113°–118° C./25 mmHg.

NMR Absorption Spectrum of Product (CCl$_4$, δ): 6.04 (dd, 1H), 5.18–4.75 (m, 2H), 4.10 (q, 2H), 3.25 (bs, 1H), 2.20, 2.13 (ds, 3H), 1.23 (t, 3H), 1.19 (s, 6H).

To a solution of 0.195 g of cupric acetate and 0.309 g of n-butylamine in 3.3 g of dimethylformamide was added a solution of 3.0 g of ethyl 2-acetyl-3,3-dimethyl-4-pentenoate dissolved in 4.8 g of carbon tetrachloride. The reaction system was purged with argon and sealed, and the mixture was then heated at a temperature of 120° C. for 23 hours. After completion of the heating, the reaction mixture was diluted with diethyl ether, washed successively with water, 1N hydrochloric acid, an aqueous solution of sodium bicarbonate, and an aqueous solution of sodium chloride. The mixture was dried over anhydrous magnesium sulfate and distilled to give 3.6 g (conversion ratio, 89%; conversion yield, 75%) of ethyl 2-acetyl-4,6,6,6-tetrachloro-3,3-dimethylhexanoate, boiling point 108°–120° C./0.1 mmHg.

NMR Absorption Spectrum of Product (CCl$_4$, δ): 4.63 (m, 1H), 4.20 (q, 2H), 3.90 (bs, 1H), 3.16 (m, 2H), 2.23, 2.20 (ds, 3H), 1.4–1.0 (m, 9H).

EXAMPLES 2 TO 8

Synthesis of Ethyl
2-Acetyl-4,6,6,6-tetrachloro-3,3-dimethylhexanoate
with other Salt/Amine Complexes The metal salt (0.7 mmol) shown in Table I below and n-butylamine (2.8 mmols) were dissolved in 2.2 g of the solvent shown in Table I (DMF means dimethylformamide), and to the resulting solution was added a solution of ethyl 2-acetyl-3,3-dimethyl-4-pentenoate (10 mmols) dissolved in carbon tetrachloride (20 mmols). The reaction system was purged with argon and sealed, and the mixture was then heated at a temperature of 110°–120° C. for 23 hours. After completion of heating, the reaction mixture was diluted with diethyl ether, washed successively with water, 1N hydrochloric acid, an aqueous solution of sodium bicarbonate, and an aqueous solution of sodium chloride. The reaction mixture was dried over anhydrous magnesium sulfate and analyzed by gas chromatography for ethyl 2-acetyl-4,6,6,6-tetrachloro-3,3-dimethylhexanoate. The yields are shown in Table I. The NMR Spectrum of the Product thus obtained in each case was found to be quite consistent with that of the product obtained in Example 1.

TABLE I

| Example No. | Metal Salt | Solvent | Conversion Ratio (%) | Conversion Yield (%) |
|---|---|---|---|---|
| 2 | Cuprous Oxide | DMF | 93 | 74 |
| 3 | Cupric Chloride | DMF | 91 | 76 |
| 4 | Copper Oxalate | DMF | 95 | 75 |
| 5 | Copper Hydroxide | DMF | 94 | 83 |
| 6 | Ferric Chloride | DMF | 86 | 54 |
| 7 | Ferrous Oxalate | DMF | 87 | 66 |
| 8 | Cupric Acetate | Water | 70 | 66 |

EXAMPLE 9

Synthesis of Ethyl
2-Acetyl-4-bromo-6,6,6-tetrachloro-3,3-dimethylhexanoate

To a solution of 0.255 g of cupric acetate and 0.408 g of n-butylamine in 4.4 g of dimethylformamide was added a solution of 3.96 g of ethyl 2-acetyl-3,3-dimethyl-4-pentenoate dissolved in 7.92 g of carbon monobromotrichloride. The reaction system was purged with argon and sealed, and the mixture was then heated at a temperature of 110°–116° C. for 20 hours. After completion of heating, the reaction mixture was diluted with diethyl ether and washed successively with water, 1N hydrochloric acid, an aqueous solution of sodium bicarbonate, and an aqueous solution of sodium chloride. The mixture was dried over anhydrous magnesium sulfate and distilled to give 2.6 g (33% yield) of ethyl 2-acetyl-4-bromo-6,6,6-trichloro-3,3-dimethylhexanoate, boiling point 109°–113° C./0.2–0.3 mmHg.

NMR Absorption Spectrum of Product (CCl$_4$, δ): 4.36 (m, 1H), 4.13 (q, 2H), 3.3–2.9 (m, 3H), 2.37, 2.15 (ds, 3H), 1.55–1.05 (m, 9H).

EXAMPLE 10

Synthesis of Ethyl 2-(2,2-Dichlorovinyl)-3,3-dimethylcyclopropanecarboxylate Sodium (0.6 g) was dissolved in 10 ml of absolute ethanol, and the ethanol was then distilled off under reduced pressure. To the residue suspended in 10 ml of anhydrous tetrahydrofuran was slowly added a solution of 2.29 g of ethyl 2-acetyl-4,6,6,6-tetrachloro-3,3-dimethylhexanoate dissolved in 5 ml of anhydrous tetrahydrofuran, while the reaction mixture was cooled with ice. The mixture was stirred for 30 minutes and then stirred at room temperature for 5 hours. The mixture was rendered neutral with an ethereal solution of hydrogen chloride while cooled with ice and then washed successively with water and an aqueous solution of sodium chloride. The resulting mixture was dried over anhydrous magnesium sulfate and distilled to to give 0.92 g (60% yield) of ethyl 2-(2,2-dichlorovinyl)-3,3-dimethylcyclopropanecarboxylate, boiling point 94°–96° C./1.5 mmHg.

NMR Absorption Spectrum of Product (CCl$_4$, $\delta$): 6.23, 5.57 (dd, 1H), 4.07 (q, 2H), 2.27–1.45 (m, 2H), 1.37–1.13 (m, 9H).

In the NMR spectrum, absorptions due to the presence of a cis-isomer and a trans-isomer in the product were observed at 6.23 and 5.57, respectively, as doublets and, from the ratio of absorption strength thereof, the ratio of cis-form to trans-form was found to be 4:6.

EXAMPLE 11

Synthesis of Ethyl 2-Acetyl-4,6,6,6-tetrachloro-3-phenylhexanoate

The starting material was prepared as follows. To a mixture of 4.02 g of cinnamyl alcohol and 6.6 g of ethyl $\beta$-ethoxycrotonate was added 10 mg of phosphoric acid. The resulting mixture was heated to a temperature of 150° C. over a period of about 40 minutes and then heated at 150° C. for 4 hours with stirring while the ethanol formed during the reaction was distilled off. Thereafter, the reaction mixture was distilled to give 6.3 g (81% yield) of ethyl 2-acetyl-3-phenyl-4-pentenoate, boiling point 170°–174° C./20 mmHg.

The product thus obtained showed complicated spectra, since it was an equilibrium mixture of keto and enol forms.

NMR Absorption Spectrum was as follows (CCl$_4$, $\delta$): 7.17 (s, 5H), 6.22–5.60 (m, 1H), 5.18–4.78 (m, 2H), 4.30–3.65 (m, 4H), 2.20, 1.90 (ds, 3H), 1.35–0.78 (m, 3H).

To a solution of 0.255 g of cupric acetate and 0.408 g of n-butylamine in 4.4 g of dimethylformamide was added a solution of 5.2 g of ethyl 2-acetyl-3-phenyl-4-pentenoate dissolved in 6.2 g of carbon tetrachloride. The reaction system was purged with argon and sealed, and the mixture was heated at a temperature of 110° to 116° C. for 20 hours. The reaction mixture then was diluted with diethyl ether and washed successively with water, 1N hydrochloric acid, an aqueous solution of sodium bicarbonate, and an aqueous solution of sodium chloride. The mixture was dried over anhydrous magnesium sulfate and distilled to give 5.7 g (conversion ration, 93%; conversion yield, 77%) of ethyl 2-acetyl-4,6,6,6-tetrachloro-3-phenylhexanoate, boiling point 144°–146° C./0.3 mmHg.

Infrared Absorption Spectrum of Product (cm$^{-1}$): 1734, 1720, 1176, 795, 760, 705.

EXAMPLE 12

Synthesis of Ethyl 2-(2,2-Dichlorovinyl)-3-phenylcyclopropanecarboxylate

Sodium 0.6 g was dissolved in 10 ml of absolute ethanol, and the ethanol was then distilled off under reduced pressure. To the residue suspended in 10 ml of anhydrous tetrahydrofuran was slowly added a solution of 2.6 g of ethyl 2-acetyl-4,6,6,6-tetrachloro-3-phenylhexanoate dissolved in 5 ml of anhydrous tetrahydrofuran, while the reaction mixture was cooled with ice-sodium chloride. The mixture was stirred for 1 hour and then stirred at room temperature for 4 hours. The mixture was then rendered neutral with an etheral solution of hydrogen chloride, while cooled with ice and washed successively with water and an aqueous solution of sodium chloride. The resulting mixture was dried over anhydrous magnesium sulfate and distilled to give 1.12 g (61% yield) of ethyl 2-(2,2-dichlorovinyl)-3-phenylcyclopropanecarboxylate, boiling point 130°–135° C./0.2 mmHg.

The NMR spectrum of the product thus obtained showed at least 3 structural isomers. These structural isomers could be distinguished from each other by the different absorption values of the olefinic hydrogen in the following NMR absorption spectrum (CCl$_4$, $\delta$): 7.2 (bs, 5H), 6.10 (d, 0.35H), 5.50 (d, 0.30H), 5.13 (d, 0.35H), 4.40–3.65 (m, 2H), 3.10–1.90 (m, 3H), 1.50–0.85 (m, 3H).

EXAMPLE 13

Synthesis of Ethyl 2-Benzoyl-4,6,6,6-tetrachloro-3,3-dimethylhexanoate

To a solution of 0.13 g of cupric acetate and 0.2 g of n-butylamine in 2.2 g of dimethylformamide was added a solution of 2.6 g of ethyl 2-benzoyl-3,3-dimethyl-4-pentenoate dissolved in 3.2 g of carbon tetrachloride. The reaction system was purged with argon and sealed, and the mixture was then heated at a temperature of 110° C. for 21 hours. The reaction mixture was then diluted with diethyl ether and washed successively with water, 1N hydrochloric acid, an aqueous solution of sodium bicarbonate, and an aqueous solution of sodium chloride. The mixture was dried over anhydrous magnesium sulfate and distilled to yield 2.0 g (conversion ration, 75%; conversion yield, 64%) of ethyl 2-benzoyl-4,6,6,6-tetrachloro-3,3-dimethylhexanoate, boiling point 148°–165° C./0.15–0.35 mmHg.

NMR Absorption Spectrum of Product (CCl$_4$, $\delta$): 8.02–7.80 (m, 2H), 7.65–7.20 (m, 3H), 5.1–4.6 (m, 2H), 4.10 (dq, 2H), 3.3–3.0 (m, 2H), 1.5–1.0 (m, 9H).

EXAMPLE 14

Synthesis of Ethyl 2-(2,2-Dichlorovinyl)-3,3-dimethylcyclopropanecarboxylate Sodium (0.37 g) was dissolved in 7 ml of absolute ethanol, and the ethanol was then distilled off under reduced pressure. To the residue suspended in 6 ml of anhydrous tetrahydrofuran was slowly added a solution of 1.66 g of ethyl 2-benzoyl-4,6,6,6-tetrachloro-3,3-dimethylhexanoate in 2 ml of anhydrous tetrahydrofuran, while the reaction mixture was cooled in ice-/sodium chloride. The mixture was stirred for 30 minutes and then stirred at room temperature for 3 hours. The mixture was rendered neutral with an ethereal solution of hydrogen chloride, while cooled with ice, and washed successively with water and an aqueous solution of sodium chloride. The resulting mixture was dried over anhydrous magnesium sulfate and distilled to give 0.45 g (47% yield) of ethyl 2-(2,2-dichlorovinyl)-3,3-dimethylcyclopropanecarboxylate, boiling point 90°–104° C./2 mmHg.

The NMR Spectrum of the product thus obtained was quite consistent with that of the product obtained in Example 10 and showed that the product contained a ratio of cis to trans forms of 4:6.

EXAMPLE 15

Synthesis of Isopropyl 2-Acetyl-4,6,6,6-tetrachloro-3,3-dimethylhexanoate

To a solution of 0.098 g of cupric acetate and 0.154 g of n-butylamine in 1.65 g of dimethylformamide was added a solution of 1.59 g of isopropyl 2-acetyl-3,3-dimethyl-4-pentenoate in 2.4 g of carbon tetrachloride. The reaction system was purged with argon and sealed, and the mixture was heated at a temperature of 110° C. for 17 hours. The reaction mixture was then diluted with diethyl ether and washed successively with water, 1N hydrochloric acid, an aqueous solution of sodium bicarbonate, and an aqueous solution of sodium chloride. The mixture was dried over anhydrous magnesium sulfate and distilled to give 1.65 g (conversion ratio, 87%; conversion yield 69%) of isopropyl 2-acetyl-4,6,6,6-tetrachloro-3,3-dimethylhexanoate, boiling point 103°–113° C./0.15 mmHg.

NMR Absorption Spectrum of Product (CCl$_4$, δ): 5.03 (m, 1H), 4.72–4.49 (m, 1H), 3.86 (bs, 1H), 3.18–3.02 (m, 2H), 2.20, 2.17 (ds, 3H), 1.33–1.07 (m, 2H).

EXAMPLE 16

Synthesis of Isopropyl 2-(2,2-Dichlorovinyl)-3,3-dimethylcyclopropanecarboxylate Sodium (0.3 g) was dissolved in 10 ml of anhydrous isopropyl alcohol, and the isopropyl alcohol was then distilled off under reduced pressure. To the residue suspended in 5 ml of anhydrous tetrahydrofuran was slowly added 1.2 g of isopropyl 2-acetyl-4,6,6,6-tetrachloro-3,3-dimethylhexanoate, while the reaction mixture was cooled with ice/sodium chloride. The mixture was stirred for 30 minutes and then stirred at room temperature for 4 hours. Thereafter, the mixture was heated at a temperature of 50° C. for 11 hours with stirring, rendered neutral with an ethereal solution of hydrogen chloride, while cooled with ice, and washed successively with water and an aqueous solution of sodium chloride. The mixture was dried over anhydrous magnesium sulfate and distilled to give 0.4 g (49% yield) of isopropyl 2-(2,2-dichlorovinyl)-3,3-dimethylcyclopropanecarboxylate, boiling point 96°–104° C./3.5 mmHg.

NMR Absorption Spectrum of Product (CCl$_4$, δ): 6.20, 5.53 (dd, 1H), 4.90 (m, 1H), 2.23–1.40 (m, 2H), 1.27–1.18 (m, 12H).

In the NMR spectrum, absorptions due to the presence of a cis-isomer and a trans-isomer in the product were observed at 6.20 and 5.53, respectively, as doublets and, from the ratio of absorption strengths, the ratio of cis- to trans-form was found to be 4:6.

The conversion of compounds of formulas (IV) and (VI) to cyclopropanecarboxylates of formula (I) is illustrated in the following examples.

EXAMPLE 17

Deacylation of Ethyl 1-Acetyl-2-(2,2-dichlorovinyl)-3,3-dimethylcyclopropanecarboxylate, a Compound of Formula (IV)

Sodium (0.083 g) was dissolved in 2 ml of absolute ethanol, and the ethanol was then distilled off under reduced pressure. To the residue in 5 ml of tetrahydrofuran was added, while the reaction mixture was cooled with ice, a solution of 0.834 g of ethyl 1-acetyl-2-(2,2-dichlorovinyl)-3,3-dimethylcyclopropanecarboxylate in 1 ml of tetrahydrofuran. The mixture was stirred at room temperature for 5 hours and then stirred at 50° C. for 30 minutes. The mixture was acidified by addition of an ethereal solution of hydrogen chloride while cooled with ice and then washed with water. The ethereal solution was dried over anhydrous magnesium sulfate and distilled to give 0.4 g (56% yield) of ethyl 2-(2,2-dichlorovinyl)-3,3-dimethylcyclopropanecarboxylate.

NMR Absorption Spectrum of the Product (CCl$_4$, δ): 6.23, 5.57 (dd, 1H), 4.07 (q, 2H), 2.27–1.45 (m, 2H), 1.37–1.13 (m, 9H).

From the ratio of absorption heights at δ6.23 and 5.57 in the NMR spectrum, the ratio of cis- to transisomer in the product was found to be 4:6.

EXAMPLE 18

Deacylation and Dehydrohalogenation of Ethyl 1-Acetyl-2-(2,2,2-trichloroethyl)-3,3-dimethylcyclopropanecarboxylate, A Compound of Formula (VI)

Sodium (0.32 g) was dissolved in 5 ml of absolute ethanol, and then the ethanol was distilled off under reduced pressure. To the residue in 5 ml of tetrahydrofuran was added, while the reaction mixture was cooled with ice, 1.42 g (crude impure material) of ethyl 1-acetyl-2-(2,2,2-trichloroethyl)-3,3-dimethylcyclopropanecarboxylate. The mixture was stirred with cooling for 30 minutes, then at room temperature for an additional 17 hours. Thereafter, the mixture was acidified by addition of an ethereal solution of hydrogen chloride, while cooled with ice, and washed successively with water and an aqueous solution of sodium chloride. The organic layer was dried over anhydrous magnesium sulfate and distilled to afford 0.3 g (28% yield) of ethyl 2-(2,2-dichlorovinyl)-3,3-dimethylcyclopropanecarboxylate, boiling point 90°–104° C./2 mmHg.

The NMR absorption spectrum of the product was identical with that described in Example 17.

By the methods described above 3-phenoxybenzyl 2-acetyl-3,3-dimethyl-4-pentenoate may be reacted with carbon tetrachloride to form 3-phenoxybenzyl 2-acetyl-4,6,6,6-tetrachloro-3,3-dimethylhexanoate, which in turn may be reacted with sodium isopropoxide or sodium t-butoxide to yield 3-phenoxybenzyl 2-(2,2-dichlorovinyl)-3,3-dimethylcyclopropanecarboxylate.

It is apparent that examples of the process of this invention may be multiplied indefinitely without departing from the scope of the invention as defined in the following claims.

We claim:

1. A process for preparing a dihalovinylcyclopropanecarboxylate represented by the formula

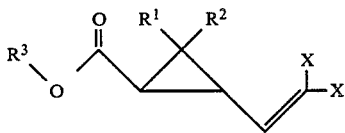

wherein $R^1$ and $R^2$ each independently represent a hydrogen atom or a hydrocarbon group; $R^3$ represents a lower alkyl group or a group of the formula

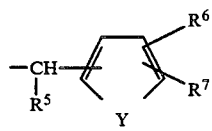

wherein Y represents an oxygen atom, a sulfur atom or a —CH=CH— group, $R^5$ represents a hydrogen atom or a cyano group, $R^6$ represents a hydrogen atom, a lower alkyl group, a phenoxy group, a benzyl group or a thiophenyl group, and $R^7$ represents a hydrogen atom or a lower alkyl group; and X represents a halogen atom; which comprises reacting a compound represented by the formula

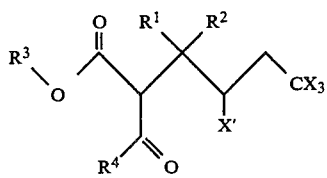

wherein $R^1$, $R^2$, $R^3$, and X are as defined above, and X' is a halogen of atomic number equal to or lower than X, and $R^4$ represents a hydrogen atom, a lower alkyl group or a phenyl group, with an alkali metal alkoxide in an ether type solvent.

2. A process of claim 1 in which $R^1$, $R^2$, and $R^4$ each independently is hydrogen, lower alkyl, or phenyl, $R^3$ is lower alkyl, 3-phenoxybenzyl, α-cyano-3-phenoxybenzyl, or 5-benzyl-3-furylmethyl, X is chlorine, bromine or fluorine, and X' is chlorine or bromine.

3. The process of claim 2 in which $R^1$, $R^2$, and $R^4$ each is methyl.

4. The process of claim 3 in which X and X' each is chlorine.

5. The process of claim 3 in which $R^3$ is lower alkyl.

6. The process of claim 1 in which the compound of formula (II) is prepared by adding a carbon tetrahalide to an α-acyl-γ-unsaturated carboxylate represented by the formula

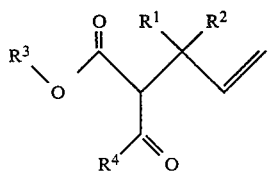

in the presence of a copper or iron salt and an organic amine.

7. The process of claim 6 in which the carbon tetrahalide is carbon tetrachloride, carbon tetrabromide, or bromotrichloromethane, $R^1$, $R^2$, and $R^4$ each is methyl, and $R^3$ is lower alkyl.

8. Process as in claim 1 in which the amount of base is in excess of 2 mol equivalents.

9. Process as in claim 1 in which the amount of base is at least 3 mol equivalents.

10. Process as in claim 9 in which said solvent is tetrahydrofuran.

11. Process as in claim 10 in which said alkali metal alkoxide is sodium ethoxide.

12. Process as in claim 10 in which said alkali metal alkoxide is sodium methoxide.

13. Process as in claim 8 in which $R^1$, $R^2$, and $R^4$ are each methyl, $X^1$ and X are each chlorine and R is lower alkyl.

14. Process as in claim 13 in which the amount of base is at least 3 mol equivalents and the solvent is tetrahydrofuran.

15. A process for preparing a dihalovinylcyclopropanecarboxylate represented by the formula

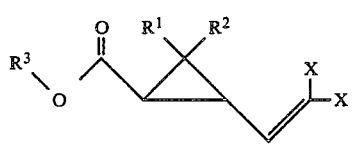

where $R^1$ and $R^2$ each independently represents a hydrogen atom or a hydrocarbon residual group; $R^3$ represents a lower alkyl group or a group of the formula

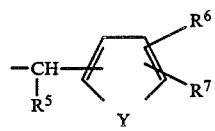

wherein Y represents an oxygen atom, a sulfur atom or a —CH=CH— group, $R^5$ represents a hydrogen atom or a cyano group, $R^6$ represents a hydrogen atom, a lower alkyl group, a phenoxy group, a benzyl group or a thiophenyl group, and $R^7$ represents a hydrogen atom or a lower alkyl group; and X represents a halogen atom; which comprises reacting a compound represented by the formula

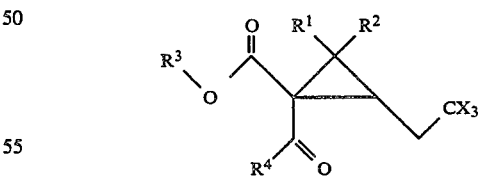

wherein $R^1$, $R^2$, $R^3$, and X are as defined above, and $R^4$ represents a hydrogen atom, a lower alkyl group or a phenyl group, with an alkali metal alkoxide in an ether type solvent.

16. Process as in claim 15 in which the amount of base is in excess of 2 mol equivalents.

17. Process as in claim 16 in which said solvent is tetrahydrofuran.

* * * * *